United States Patent [19]

Kruger et al.

[11] Patent Number: 4,644,575
[45] Date of Patent: Feb. 17, 1987

[54] ELECTRONIC SLIT COLLIMATION

[75] Inventors: Robert A. Kruger, Sandy; James A. Sorenson, Salt Lake City, both of Utah

[73] Assignee: University of Utah, Salt Lake City, Utah

[21] Appl. No.: 673,844

[22] Filed: Nov. 21, 1984

[51] Int. Cl.$^4$ ............................................. H05G 1/64
[52] U.S. Cl. ...................................... 378/99; 358/111
[58] Field of Search .................... 378/7, 12, 19, 99; 358/111

[56] References Cited

U.S. PATENT DOCUMENTS

| 4,436,095 | 3/1984 | Kruger | 378/99 |
| 4,468,697 | 8/1984 | Verhoeven | 378/99 |
| 4,493,096 | 1/1985 | Rieke | 378/99 |
| 4,549,307 | 10/1985 | Macovski | 378/99 |

Primary Examiner—Craig E. Church
Assistant Examiner—John C. Freeman
Attorney, Agent, or Firm—Brady, O'Boyle & Gates

[57] ABSTRACT

A slit collimation system includes a signal absorptive plate assembly having a narrow slit located between a source of x-ray radiation and an object such as a patient undergoing a diagnostic imaging procedure. An image intensifier tube is located on the other side of the object and is optically coupled to an imaging device such as a television camera. The camera generates an image of the slit as well as x-ray scatter in succeeding TV frames as the slit is scanned, i.e. moved linearly over the object. Each TV frame is digitized and fed into a recursive loop including a digital memory adapted to store a complete TV frame which is comprised of an array of pixels. Pixel intensity values of successive frames are logically combined so that the video information in the shadow of the slit is accepted while the remainder of the video information which includes scatter and noise is rejected resulting in an x-ray image which is free of scatter.

15 Claims, 4 Drawing Figures

ELECTRONIC SLIT COLLIMATION

BACKGROUND OF THE INVENTION

1. Field of the Invention

This invention relates generally to radiographic apparatus and more particularly to apparatus for removing x-ray scatter during radiographic imaging.

2. Description of the Prior Art

When one exposes an object, such as a patient, to x-rays during a diagnostic imaging procedure, the x-ray tube assembly acts like a point source whereupon x-rays are emitted in a straight line. They then pass through the patient and impinge on a detector, which in the case of fluoroscopy, comprises electronic imaging apparatus such as an image intensifier coupled to a television camera. The x-rays that pass through the patient in a straight line are known as primary x-rays and are those desired to be detected. Other x-rays, known as scatter, in passing through the patient emerge at widely different divergent angles and are normally suppressed insofar as possible. There are a number of existing techniques for discriminating between primary and scattered radiation. The most common means is to utilize an anti-scatter grid which is placed behind or under the patient and in front of the detector. The anti-scatter grid is comprised of, for example, a series of lead or tantalum or other heavy metal strips that are laminated to form a plurality of parallel septa which permit x-rays to pass through if they are more or less parallel to the septa but x-rays which pass through at divergent angles have to pass through the lead or heavy metal and are thus attenuated. Disadvantages of an anti-scatter grid are several; first, it is far from perfect and still permits some scattered radiation to reach the detector. Second, a portion of the primary radiation also is removed, meaning that the total amount of radiation delivered to the body undergoing a radiographic procedure must be increased to compensate for that lost in the anti-scatter grid, meaning that whenever the primary radiation is attenuated or scattered radiation is detected, it is necessary to increase the x-ray dose to the body in order to obtain the same statistical information out of the image. Thus a trade off has normally existed between the loss of primary radiation, the x-ray dose and the removal of scatter.

Another known method that has been used to remove x-ray scatter employs a pair of thin slits, constructed of strongly x-ray attenuating material. One slit (foreslit) is placed between the x-ray source (tube) and the object (patient) being imaged. The second, a larger slit (aftslit) is placed behind or beneath the object (patient) and ahead of the detector. The slits are precisely aligned so that x-rays that pass in a straight line from the source and through the foreslit, also will pass through the aftslit if the x-rays are not scattered within the object (patient). X-rays that are scattered within the patient are most likely to strike the x-ray absorbing material contained within the aftslit. An image of an extended object is made by scanning the x-ray source, foreslit and aftslit in synchronism. Additionally, a plurality of paired slits have also been used. This method of scanning paired or multiple paired slits is intrinsically more efficient in rejecting scattered radiation than the use of an anti-scatter grid, but also is more complicated. A significant disadvantage of this method is that due to the relatively great weight and bulk of the aftslit, scanning and alignment of the paired slit assemblies present a substantial mechanical problem. Additional space is also required between the patient and the image receptor for the aftslit assembly, which causes undesirable magnification of the image and, usually, a specially constructed or modified patient support table is needed.

Accordingly, it is an object of the present invention to provide an improvement in apparatus for making a radiographic image.

It is another object of the invention to provide an improvement in the ratio of the primary radiation to the scatter radiation in an image generated during a diagnostic imaging procedure.

It is a further object of the invention to remove the anti-scatter grid assembly normally located between an object receiving x-ray radiation and an x-ray detector.

It is still another object of the invention to electronically collimate x-ray radiation for removing scatter during a radiographic imaging procedure.

SUMMARY

Briefly, the foregoing and other objects are achieved in accordance with electronic slit collimation apparatus comprising, among other things, means for providing a scanned narrow slit or multiple slits or apertures of other shapes between an x-ray source and object, such as a patient, undergoing a diagnostic imaging procedure. Additionally, means, including a detector, are located on the other side of the object for electronically rejecting x-ray image information that falls outside of the slit while retaining that inside of the slit. The detector, for example, includes an image intensifier tube coupled to a TV imaging system which produces a frame every 1/30th of a second as the slit moves across the object. Each frame including an image of the slit is digitized and fed to a recursive loop including a digital memory capable of storing video information of each pixel signal of an array of pixels in each frame. Successive frames are added together with the video information within each frame that lies within the shadow of the slit being accepted while rejecting all other video information outside of the slit. Since the video signal within the slit is much more intense than that outside the slit, discrimination between intensity levels is achieved electronically to elminate the scatter and thus obviate the need for the bulky aftslit assembly or the anti-scatter grid.

BRIEF DESCRIPTION OF THE DRAWING

While the present invention is defined in the claims annexed to and forming a part of this specification, a better understanding can be had by reference to the following description when taken in conjunction with the accompanying drawings in which:

DESCRIPTION OF THE PREFERRED EMBODIMENT

Figure 1:
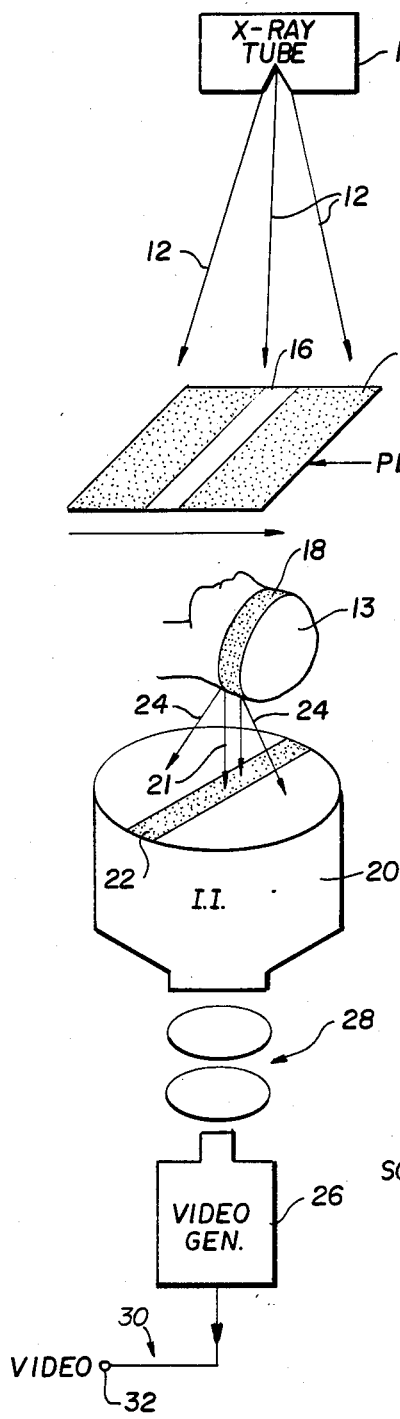
FIG. 1 is a simplified diagram partially illustrative of the preferred embodiment of the invention.

Referring now to the drawings and more particularly to FIG. 1, reference numeral 10 denotes a source of radiation such as an x-ray tube assembly which acts as a point source whereby x-rays 12 are emitted in a straight line toward an object 13, such as a patient undergoing a diagnostic imaging procedure. Above the patient is located a relatively flat plate 14 comprised of x-ray absorbent material such as lead, for example, and which includes a generally rectangular slit 16 which provides an aperture through which x-rays 12 pass to the patient 13. Further as shown in FIG. 1, the slit 16 is transverse to the patient's head with the plate 14 being moved in a scanning motion longitudinally from left to right.

Figure 3:
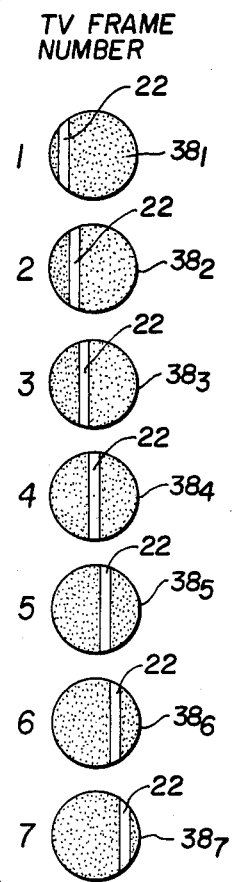
FIG. 3 is a set of TV frames illustrative of the slit being scanned by the apparatus shown in FIG. 1.
Figure 2:
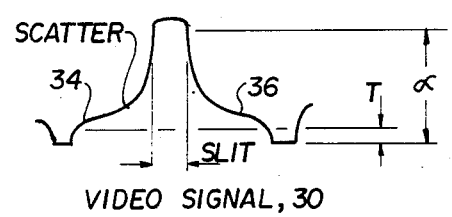
FIG. 2 is a depiction of the analog video signal generated by the apparatus shown in FIG. 1.

Accordingly, x-rays 12 from the source 10 enter the object or patient 13 from the slit 16 in a relatively narrow band or fan beam 18 defined by the dimensions of the slit 16 and the relative spacing of the plate 14 between the patient and the x-ray tube 10. Typically, the beam 18 would be 20 centimeters wide by 1.0 centimeters across. The x-rays emerging from the patient's head are detected, for example, by an x-ray image intensifier 20 with the primary x-rays 21 impinging thereon to form a shadow image 22 of the slit 16 as well as scatter x-rays which are directed at widely divergent angles as shown by reference numeral 24. The image output of the image intensifier 20 is coupled to a video generator 26, such as a TV camera, by means of an optical system 28 and operates to successively form a new TV image or frame every 1/30 of a second. The video signal output of the TV camera 26 comprises an analog signal which is shown in FIG. 2 by reference numeral 30 and would appear, for example, at an output terminal 32. The analog video signal 30 of one line of a frame as shown includes a relatively large amplitude portion which comprises the video signal of the slit 16 while the signal due to scattered x-ray and ambient light comprises relatively low amplitude portions 34 and 36 on either side of the slit portion 32. It can further be seen in FIG. 3 that successive frames 1 through 7 of the analog video signal 30 will provide an image 22 of the slit during translation of the collimator member 14 from left to right as shown in the frames $38_1, 38_2 \ldots 38_6, 38_7$.

Whereas the prior art relied on one or more mechanical devices for removing the scattered x-rays 24 emerging from the patient 13 during a diagnostic imaging procedure, the present invention, as will now be shown, provides an electronic means for discriminating between video signal levels inside and outside of the image 22 of the slit in order to eliminate unwanted x-ray scatter as well as noise.

Figure 4:
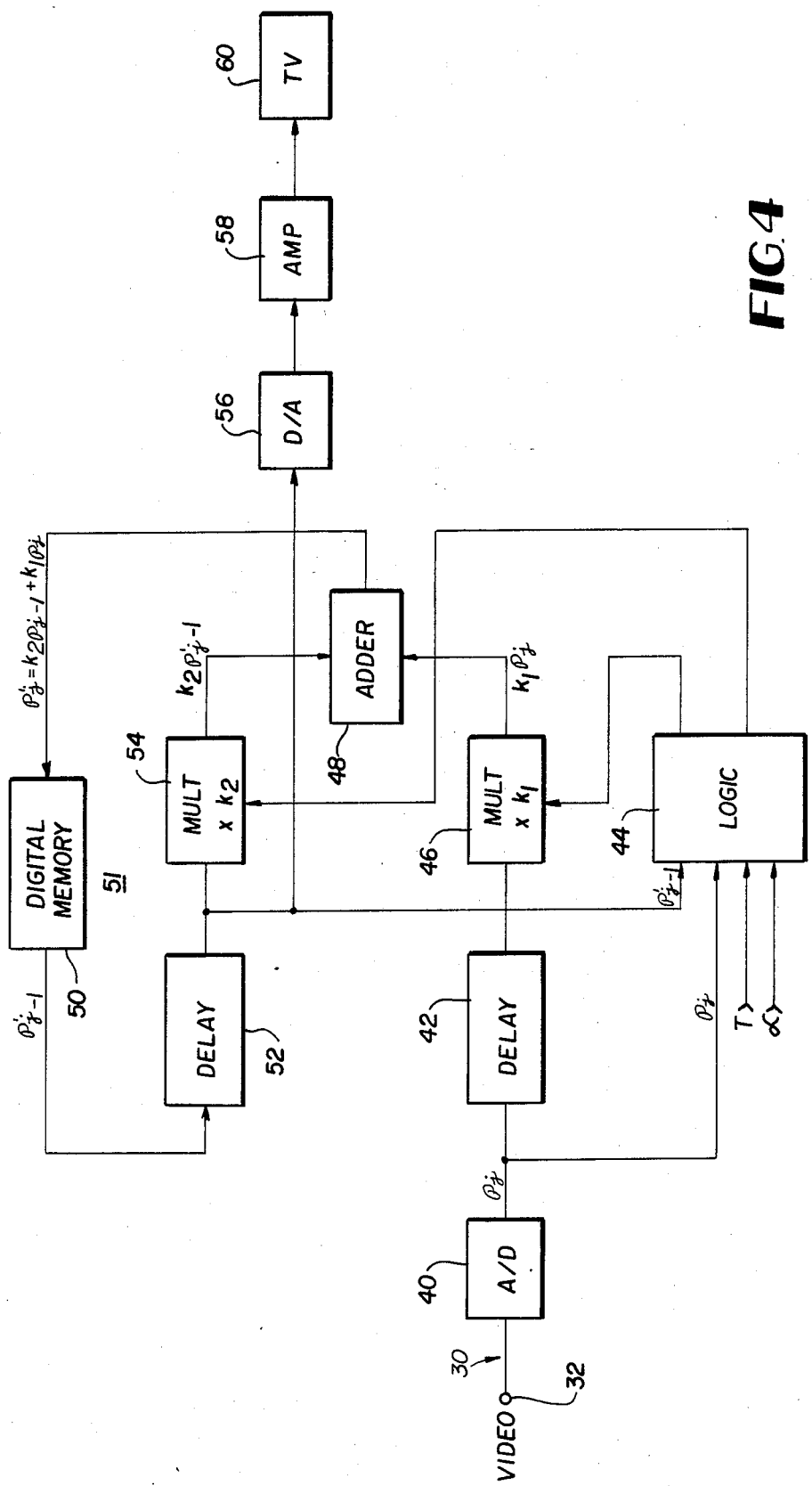
FIG. 4 is an electrical block diagram further illustrative of the preferred embodiment of the invention.

Referring now to FIG. 4, each TV frame is comprised of a matrix array of picture elements (pixels) of analog video information 30 appearing at the output terminal 32 of the TV camera 26. Each pixel signal is fed to an analog to digital converter 40 where the brightness level of each pixel of the video frame is digitized. Each digital signal of a pixel comprises, for example, an eight bit digital pulse signal p representative of one of a plurality (typically 256) graduations of luminance level. Thus the A/D converter 40 outputs a serial pulse train of digital signals $p_n$ as each frame of n frames is generated by the TV camera 26.

Letting $p_j(x, y)$ be the digital pixel value, i.e. video signal amplitude, appearing at terminal 32 during the jth frame at the spatial location (x, y) of the image and $p'_j(x, y)$ be the pixel value fed to a memory 50 for storing an image frame following the end of the jth frame, each incoming digital pixel signal comprises the signal $p_j$ which is commonly coupled to time delay means 42 such as a delay line as well as a logic circuit 44. The output of the delay circuit means 42 is fed to a digital multiplier 46 which applies a multiplying factor $k_1$ to the signal $p_j$ in accordance with the output of the logic circuit 44, as will be explained subsequently, to provide a digital output of $k_1 p_j$. This signal is next applied to a digital adder 48 whose output comprises the signal $P'_j$ which is coupled to a digital frame store memory 50. The memory 50 has a storage capacity for storing the individual digital video signal values for each pixel of an entire TV frame or raster. Thus for a matrix array of pixels having a dimension of $n \times n$, where n is in the range of 500 to 2000, the memory 50 must include between 0.25 and 4.0 megabytes of storage. Such apparatus is well known to those in the art and is commercially available. A typical example comprises a digital frame store manufactured by Thompson CSF Broadcast, Inc. and identified as a Model FS-963155 digital video frame store.

The frame store memory 50 is part of a recursive loop 51 which in addition to the adder 48 also includes the second digital delay device 52 and a digital multiplier 54 which is operable to apply a multiplier factor $k_2$, as controlled by the logic circuit 44, to digital output signals $p'_j$ following a delay introduced by the second delay circuit means 52. The two time delay devices 42 and 50 are provided to equalize processing time so that the output $k_2 p'_j$ of the multiplier 54 when fed to the adder 48 is in synchronism with the signal $k_1 p_j$.

The pixel signals $p'_{j-1}$ out of the frame store memory during the jth frame 50 in addition to being fed to the delay circuit 52 and then to the digital multiplier 54, are applied to the logic circuit 44 for determining the values of $k_1$ and $k_2$ along with the signals $p_j$ and two threshold signals T and $\alpha$, which will be considered subsequently. The memory output pixel signals $p'_{j-1}$ also comprise the output signal which is reconverted to an analog video signal by a digital to analog converter 56 which is subsequently amplified by amplification circuitry 58 where it is then fed to a display device such as a TV monitor 60.

In operation, incoming pixel signal values $p_j$ of the jth frame are weighted or multiplied by the factor $k_1$ and added to any previous same location pixel values $p'_{j-1}$ previously stored in memory but now weighted by the factor $k_2$. The combined pixel values $k_2 p'_{j-1} + k_1 p_j$ are set into memory as $p'_j$. The first TV frame, however, which may be, for example frame $38_1$ shown in FIG. 1, is digitized and stored in a serial sequence, pixel by pixel, in the frame store memory 50 via the multiplier 46 and the adder 48 by setting $k_1 = 1$ and $k_2 = 0$. Any input to the multiplier 54 is thus deleted because $k_2 p'_{j-1}$ will be zero. The memory 50 has its pixel addresses (x, y) synchronized with the pixel addresses of the remaining part of the system including the logic circuit 44 by driving the addresses from a common sync and clock signal, not shown. As new subsequent frame digital pixel values $p'_j$ are read into the memory 50 from the adder 48, the pre-existing values $p'_{j-1}$ are simultaneously reapplied through the time delay circuit 52 and the multiplier 54. Thus by initially setting the $k_2$ multiplier value to zero any pre-existing frame store values are deleted. Accordingly, during the first frame only the $p_j$ pixel elements multiplied by the factor $k_1$ are set into memory as $p'_j$. Thereafter, each subsequent frame is added to the preceding frame on a pixel-by-pixel basis depending upon the multiplication factors $k_1$ and $k_2$. The contents of the memory 50 are updated to $p'_{j+1}$ in each succeeding frame using the data collected during the $j^{th}$ frame in accordance with the relation:

$$p'_j \geqq k_1 p_j + k_2 p_{j-1} \qquad (1)$$

Although a position dependent logic or a brightness dependent logic may be employed, in the preferred embodiment of the invention shown in FIG. 2, the logic section 44 operates in accordance with brightness dependent logic for setting $k_1 \geqq 0$ and $k_2 \leqq 1$, where $k_1 + k_2 = 1$, for pixel signals at the spatial locations which lie outside of the shadow 22 of the slit 16 and typically $k_1 = 1$ and $k_2 = 0$ when it is within the shadow of the slit.

The logic circuit 44 is responsive to the incoming pixel data signals $p_j$, the previously stored pixel data signals $p'_{j-1}$, and at least one amplitude threshold parameter T which comprises a pre-selected value setting an absolute minimum threshold for providing signal discrimination between brightness levels in and out of the slit 16. However, to reliably discriminate between inside of the slit versus outside of the slit pixel brightness levels, a second threshold parameter $\alpha$ is preferably utilized such that T is made relatively small and just above system noise levels as shown in FIG. 2 whereas $\alpha$ is set to some value approaching 1.0, typically 0.8. The logic 44 compares the respective pixel values $p'_{j-1}$ and $p_j$ to determine whether or not they are changing on a frame-by-frame basis and at any time that $p_j$ is greater than $p'_{j-1}$ and particularly, $$p_j \geqq p_{j-1} + T$$

then that information will be stored in memory by setting $k_1 = 1$ and $k_2 = 0$ since it constitutes image information at the location of the slit 16. Conversely, if $p_j$ begins to decrease, then it is indicative that the shadow 22 of the slit 16 is past that pixel point and such pixel signals are not to be stored. Accordingly, the values of $k_1$ and $k_2$ are changed so that $k_1 = 0$ and $k_2 = 1$.

By weighting the pixel values of $p_j$ and $P'_{j-1}$ so that pixel brightness values above the threshold values established by T and $\alpha$ are stored while other values are discarded, discrimination against the signals outside of the shadow of the slit is achieved. As the shadow 22 of the slit 16 moves from left to right on a frame-by-frame basis, the pixel values $p'_{j-1}$ at the output of the delay device 52 are coupled to the digital to analog converter 56 where a video display of that frame is generated on the TV monitor 58.

While a brightness dependent logic has been shown in FIG. 2, another way of keeping track of the position of the slit is predicting where the x, y coordinates of the slit actually are and having a knowledge of where the slit should be, the address locations of the memory are programmed to keep the data and adding it to whatever is existing in the memory or the previous value can be discarded, depending upon how much noise can be tolerated into the signal processing and basically depends upon how much the new value exceeds the old value.

If a TV image is not required, the amplifier 58 can be used to drive a laser scanner, for example, and have the image printed out on a piece of film. Still one may take the contents of the video information and generate a computer printout of the image. The present approach, moreover, makes slit scanning practical and adaptable to virtually any fluoroscopy system with an image intensifier TV camera, whereas mechanical systems must be retrofitted to the particular x-ray tables, etc. Also elimination of the slit between the patient and the image receptor minimizes unnecessary air gap and magnification.

Having thus shown and described what is at present considered to be the preferred embodiment of the invention, it should be noted that the foregoing detailed description has been made by way of illustration and not limitation. Accordingly, all modifications, alterations and changes coming within the spirit and scope of the invention as defined in the appended claims are herein meant to be included.

We claim:

1. An electronic slit collimation method for dynamically discriminating between primary and scattered radiation emerging from an object receiving radiation from a radiation source during an imaging procedure and thus eliminating the need for a mechanical anti-scatter device between the object and a radiation detector, comprising the steps of:

directing a beam of radiation through a slit type aperture included in radiation absorptive means located between a source of radiation and said object for permitting a relatively narrow fan beam of radiation to pass through said object;

moving said radiation absorptive means including said slit type aperture in a scanning motion over said object in a direction transverse to the plane of said fan beam;

detecting both primary and scattered radiation emerging from said object, said primary radiation forming a shadow of said aperture;

periodically generating a frame of video pixel signals of the detected radiation, each pixel signal having an amplitude value corresponding to the respective radiation intensity level detected at the spatial location thereof;

storing at least one frame of pixel signals;

accessing the stored frame of pixel signals on a pixel-by-pixel basis during a successive frame;

determining the relative pixel signal amplitudes of respective spatial locations; and tracking the movement of the shadow of said aperture by selectively restoring the previously stored pixel signal amplitude values in the event that the pixel signal amplitude values of said successive frame are less than the stored pixel signal amplitude values of said at least one frame, while storing the incoming pixel signal amplitude values of said successive frame when they exceed the respective stored pixel signal amplitude values of said at least one frame, and wherein said step of restoring the previous pixel signal amplitude values comprises weighting the respective stored pixel signal amplitude values of said at least one frame by a first multiplication factor and weighting the pixel signal amplitude values of said successive frame by a second multiplication factor and thereafter summing respective weighted pixel signal amplitude values of each pixel signal, and wherein said step of storing the pixel signal amplitude values of said successive frame comprises weighting the respective pixel signal amplitude values of said successive frame now by said first multiplication factor and weighting the pixel signal amplitude values of the stored frame signal by said second multiplication factor and thereafter summing respective weighted pixel signal amplitude values of each pixel signal, and wherein said first and second multiplication factors are determined in accordance with a predetermined logic function.

2. The method as defined by claim 1 wherein said first multiplication factor is greater than zero and equal to or less than unity and wherein said second multiplication factor is less than unity and equal to or greater than zero and wherein the sum of said first and second multiplication value is unity.

3. The method as defined by claim 2 wherein said first multiplication factor is equal to unity and said second multiplication factor is equal to zero.

4. The method as defined by claim 1 wherein said predetermined logic function includes a term relating to a minimum threshold value and a term relating to a maximum threshold value for providing reliable discrimination between pixel signals in and out of said aperture.

5. The method as defined by claim 4 wherein said logic expression comprises the expression $p_j \geq \alpha p_{j-1} + T$ where $p_j$ is the respective pixel signal amplitude values of said successive or jth frame, $p_{j-1}$ is the stored pixel signal amplitude values of the previous or $j-1$ frame, T is a minimum threshold value for discriminating against noise and $\alpha$ is a maximum value comprising a factor equal to or less than unity, both said $\alpha$ and T values being selectively chosen to reliably discriminate between pixel signal amplitudes in and out of said aperture.

6. An electronic slit collimating method for dynamically discriminating between primary and scattered radiation emerging from an object receiving radiation from a radiation source during an imaging procedure and thus eliminating the need for a mechanical anti-scatter device between the object and a radiation detector, comprising the steps of:

directing a beam of radiation through a slit type aperture included in radiation absorptive means located between a source of radiation and said object for permitting a relatively narrow fan beam of radiation to pass through said object;

moving said radiation absorptive means including said slit type aperture in a scanning motion over said object in a direction transverse to the plane of said fan beam;

detecting both primary and scattered radiation emerging from said object, said primary radiation forming a shadow of said aperture;

periodically generating a frame of video pixel signals of the detected radiation, each pixel signal having an amplitude value corresponding to the respective radiation intensity level detected at the spatial location thereof;

storing at least one frame of pixel signals;

accessing the stored frame of pixel signals on a pixel-by-pixel basis during a successive frame;

determining the relative pixel signal amplitudes of respective spatial locations; and tracking the movement of the shadow of said aperture by selectively restoring the pixel signal amplitude values of said stored frame in the event that the pixel signal amplitude values of said successive frame is less than said stored values while storing incoming pixel signal amplitude values of said successive frame in the event that it is greater than the corresponding stored value of said at least one frame, wherein said steps of restoring and storing include weighting the respective signal amplitude values of each successive frame by a multiplication factor $k_1$ and weighting the respective pixel signal amplitude values of each stored frame by a multiplication factor $k_2$ and where $k_1 + k_2 = 1$, the values of $k_1$ and $k_2$ being further determined in accordance with a predetermined logic function which during said restoring step makes $k_1 \cong 0$ and $0 < k_2 \leq 1$ and wherein during said storing step, makes $k_2 \cong 0$ and $0 < k_1 \leq 1$, pixel signals of the primary radiation existing in the shadow of said aperture being retained while pixel signals of scattered radiation are rejected.

7. The method as defined by claim 6 wherein said logic function comprises the function $p_j \geq \alpha p_{j-1} + T$, where $p_j$ is the respective pixel signal amplitude values of said successive or jth frame, $p_{j-1}$ is the stored pixel signal amplitude values during the previous or $j-1$ frame, T is a minimum threshold value above the noise level for discriminating against noise and $\alpha$ is a maximum value comprising a factor equal to or less than unity, both said $\alpha$ and T values providing a reliable discrimination between pixel signal amplitudes in and out of said aperture so that pixel signals of primary radiation existing at the shadow of said aperture are retained while pixel signals of scattered radiation are rejected.

8. The method as defined by claim 7 wherein $k_1 = 1$ and $k_2 = 0$ when $p_j \geq \alpha p_{j-1} + T$, and $k_1 = 0$ and $k_2 = 1$ when $p_j < \alpha p_{j-1} + T$.

9. Electronic slit collimation apparatus for discriminating between primary and scattered radiation emerging from an object during an imaging procedure where a source of radiation directs a beam of radiation towards the object and interposed radiation absorption means, including a slit type aperture oriented transversely across the object which moves between the source and object permitting a narrow beam of radiation to pass through said object to a detector which detects both primary and scattered radiation emerging from the object, comprising:

means for scanning said radiation absorption means over said object;

means for generating a video image of the detected radiation including means for generating a sequence of frames of video signals wherein each frame includes an array of pixels providing respective pixel signals;

means for retaining pixel signals of the primary radiation which forms a shadow of said slit type aperture while rejecting scattered radiation pixel signal existing outside of said shadow, said means for retaining further comprising digital storage means connected in a recursive loop and being operable to store a frame of digital pixel signals therein, said recursive loop including a first digital multiplier coupled to the output of said digital storage means and being operable to weight the pixel signals of said stored frame by a first multiplication factor, a pixel signal adder having an output coupled to the input of said storage means, said pixel signal adder further having an input coupled to the output of said first signal multiplier, a second digital signal multiplier having an input coupled to the digital pixel signals of a successive frame and being operable to weight incoming pixel signals of said successive frame by a second multiplication factor and provide an output thereof to another input of said adder, respective weighted pixels of said stored frame and said successive frame being summed together by said pixel signal adder and coupled to the input of said storage means, and logic means responsive to the respective pixel signal levels of said stored frame and said successive frame and operating in accordance with a predetermined logic expression to control the value of said first and second multiplication factors of said first and second signal multipliers such that when the amplitudes of said successive frame pixel signals are greater than the amplitudes of the stored frame pixel signals, the first multiplication factor is made less than said second multiplication factor, and vice-versa.

10. The electronic slit collimation apparatus as defined by claim 9 wherein said first and second multiplication factors have a sum equal to unity and wherein said first multiplication factor is made to be equal to or greater than zero but less than unity and said second multiplication factor is made to be greater than zero and equal to or less than unity when the signal levels of a successive frame of pixel signals is greater than the signal level of the stored frame pixel signals wherein the first multiplication factor is greater than zero and equal to or less than unity while said second multiplication factor is equal to or greater than zero but less than unity when the signal level of said successive frame pixel signals is less than the signal levels of said stored frame pixel signals.

11. The apparatus as defined by claim 10 wherein said first multiplication factor is equal to zero and said second multiplication factor is equal to unity when the level of the successive frame pixel signals is greater than the level of said stored frame pixel signals and wherein said first multiplication factor is equal to unity and said second multiplication factor is equal to zero when the level of the successive frame pixel signals is less than the level of the stored frame pixel signals.

12. The apparatus as defined by claim 9 wherein said logic expression comprises the expression $p_j \geq \alpha p_{j-1} + T$ where $p_j$ is the respective pixel signal amplitude of said successive or jth frame, $p_{j-1}$ is the stored pixel signal amplitude values of the previous or $j-1$ frame, T is the minimum threshold value above the noise level for discriminating against noise, and $\alpha$ is a maximum value comprising a factor equal to or less than unity, both said $\alpha$ and T values enabling a more reliable discrimination between pixel signal amplitudes in and out of said aperture so that the primary radiation at the shadow of said aperture is obtained while said scattered radiation is rejected.

13. Electronic slit collimation apparatus for dynamically discriminating between primary and scattered radiation emerging from an object receiving radiation from a radiation source during an imaging procedure and thus eliminating the need for a mechanical anti-scatter device between the object and a radiation detector, comprising:

means for directing a beam of radiation through a slit type aperture included in radiation absorptive means located between a source of radiation and said object for permitting a relatively narrow fan beam of radiation to pass through said object;

means for moving said radiation absorptive means including said slit type aperture in a scanning motion over said object in a direction transverse to the plane of said fan beam;

means for detecting both primary and scattered radiation emerging from said object, said primary radiation forming a shadow of said aperture;

means for periodically generating a frame of video pixel signals of the detected radiation, each pixel signal having an amplitude value corresponding to the respective radiation intensity level detected at the spatial location therof;

means for storing at least one frame of pixel signals;

means for accessing the stored frame of pixel signals on a pixel-by-pixel basis during a successive frame;

means for determining the relative pixel signal amplitudes of respective spatial locations; and means for tracking the movement of the shadow of said aperture by selectively restoring the pixel signal amplitude values of said stored frame in the event that the pixel signal amplitude values of said successive frame is less than said stored values while storing incoming pixel signal amplitude values of said successive frame in the event that it is greater than the corresponding stored value of said at least one frame and including, means for weighting the respective signal amplitude values of each successive frame by a multiplication factor $k_1$, means for weighting the respective pixel signal amplitude values of each stored frame by a multiplication factor $k_2$ and where $k_1 + k_2 = 1$, and means for implementing a predetermined logic function which operates to make $k_1 = 0$ and $0 < k_2 \leq 1$ when the pixel signal amplitudes of said successive frame is less than the respective amplitudes of the stored frame and to make $k_2 = 0$ and $0 < k_1 \leq 1$ when the pixel signal amplitudes of said successive frame is greater than the respective amplitudes of the stored frame, pixel signals of the primary radiation existing in the shadow of said aperture being retained while pixel signals of scattered radiation are rejected.

14. The apparatus as defined by claim 13 wherein said logic function comprises the function $p_j \geq \alpha p_{j-1} + T$, where $p_j$ is the respective pixel signal amplitude values of said successive or jth frame, $p_{j-1}$ is the stored pixel signal amplitude values during the previous or $j-1$ frame, T is a minimum threshold value above the noise level for discriminating against noise and $\alpha$ is the maximum value comprising a factor equal to or less than unity, both said $\alpha$ and T values providing a reliable discrimination between pixel signal amplitudes in and out of said aperture so that pixel signals of primary radiation existing at the shadow of said aperture are retained while pixel signals of scattered radiation are rejected.

15. The apparatus as defined by claim 14 wherein $k_1 = 1$ and $k_2 = 0$ when $p_j \geq \alpha p_{j-1} + T$ and $k_1 = 0$ and $k_2 = 1$ when $p_j < \alpha p_{j-1} + T$.

* * * * *